(12) United States Patent
Rashad et al.

(10) Patent No.: US 7,222,624 B2
(45) Date of Patent: May 29, 2007

(54) DUAL SENSOR OXYGEN THERAPY DEVICE

(75) Inventors: M. Abdul-Aziz Rashad, Kenmore, NY (US); Paul W. Belanger, East Amherst, NY (US); Bryan R. Bielec, Hamburg, NY (US)

(73) Assignee: Praxair Technology, Inc., Danbury, CT (US)

( * ) Notice: Subject to any disclaimer, the term of this patent is extended or adjusted under 35 U.S.C. 154(b) by 331 days.

(21) Appl. No.: 10/882,610

(22) Filed: Jul. 2, 2004

(65) Prior Publication Data

US 2006/0011199 A1 Jan. 19, 2006

(51) Int. Cl.
- *A61M 16/00* (2006.01)
- *A62B 7/00* (2006.01)
- *A61B 5/00* (2006.01)
- *A61B 5/08* (2006.01)

(52) U.S. Cl. ............ 128/204.23; 128/204.23; 128/205.11; 600/323; 600/344

(58) Field of Classification Search ........... 600/532, 600/529, 538, 300, 323, 324, 333, 340, 344; 128/204.18, 204.21, 204.23, 205.11, 205.23

See application file for complete search history.

(56) References Cited

U.S. PATENT DOCUMENTS

| | | | | |
|---|---|---|---|---|
| 4,889,116 A | * | 12/1989 | Taube | 128/204.23 |
| 5,365,922 A | * | 11/1994 | Raemer | 128/204.23 |
| 5,682,877 A | | 11/1997 | Mondry | 128/204.23 |
| 5,735,800 A | * | 4/1998 | Yasukawa et al. | 600/503 |
| 5,766,131 A | * | 6/1998 | Kondo et al. | 600/502 |
| 5,865,174 A | * | 2/1999 | Kloeppel | 128/204.23 |
| 6,186,142 B1 | * | 2/2001 | Schmidt et al. | 128/204.23 |
| 6,192,883 B1 | * | 2/2001 | Miller, Jr. | 128/204.21 |
| 6,198,951 B1 | * | 3/2001 | Kosuda et al. | 600/323 |
| 6,371,114 B1 | * | 4/2002 | Schmidt et al. | 128/204.23 |
| 6,470,885 B1 | * | 10/2002 | Blue et al. | 128/204.18 |
| 6,532,958 B1 | * | 3/2003 | Buan et al. | 128/204.23 |
| 6,551,384 B1 | * | 4/2003 | Ackley et al. | 95/96 |
| 6,629,525 B2 | * | 10/2003 | Hill et al. | 128/202.26 |
| 6,931,269 B2 | * | 8/2005 | Terry | 600/336 |
| 2002/0035315 A1 | * | 3/2002 | Ali et al. | 600/300 |
| 2004/0087846 A1 | * | 5/2004 | Wasserman | 600/323 |
| 2006/0005842 A1 | * | 1/2006 | Rashad et al. | 128/207.18 |

FOREIGN PATENT DOCUMENTS

WO    WO 02/56931 A2    7/2002

OTHER PUBLICATIONS

Fussell, et al. "Assessing Need for Long-Term Oxygen Therapy: A Comparison of Conventional Evaluation and Measures of Ambulatory Oximetry Monitoring", *Respiratory Care* Feb. 2003 vol. 48 No. 2.
John C. Chaney, et al. "Implementation of an Oxygen Therapy Clinic to Manage Users of Long-term Oxygen Therapy" *CHEST/* 122/5/Nov. 2002z.

* cited by examiner

*Primary Examiner*—Justine R. Yu
*Assistant Examiner*—Adam Brandt
(74) *Attorney, Agent, or Firm*—Robert J. Hampsch

(57) ABSTRACT

Methods and apparatus for supplying respiratory oxygen to a patient where the oxygen flow is monitored so as to be control and conserve in response to the patient's pulse rate and blood hemoglobin saturation.

8 Claims, 2 Drawing Sheets

DUAL SENSOR OXYGEN THERAPY DEVICE

FIELD OF THE INVENTION

The invention relates to devices and methods using dual sensors for monitoring and effecting conserving the delivery of oxygen to a patient.

BACKGROUND OF THE INVENTION

In the US today there exists approximately 1 million people who suffer from chronic hypoxemia as a result of having a chronic obstructive pulmonary disease (COPD). Presently there is no cure for this condition, however the detrimental impact of chronic hypoxemia is mitigated by the prescription of long term oxygen therapy (LTOT). The continuous inhalation of low flows of oxygen, typically 2–3 lpm, from a nasal cannula increases the concentration of oxygen that the patient is breathing. It is estimated that for each 1 lpm (liter per minute) flow, the overall inhaled concentration rises by 3–4%. The increase in oxygen concentration compensates for the poor function of the patient's lungs in absorbing the oxygen.

Generally when a patient is diagnosed with chronic hypoxemia, oxygen is prescribed at a fixed flow rate based on a 20 minute titration in the doctor's office. During the test, the patient's blood oxygen saturation is measured by either using an invasive blood gas analyzer or a non-invasive device known as the pulse oximeter. While measuring the blood saturation ($SpO_2$), the patient may be asked to walk on a treadmill so as to measure their need for supplemental oxygen while exerting themselves. Based on this brief test, a fixed flow of oxygen is prescribed. The patient may be advised to increase the flow rate of oxygen during the exertion, for example while climbing stairs, while sleeping or if they feel short of breath. In many cases the patient is just prescribed a flow rate of 2 lpm and then asked to come back if they continue to feel the side effects of hypoxemia which can manifest themselves as shortness of breath, headaches, nausea, etc.

Patients may be prescribed oxygen to breathe 24 hours per day or may only require oxygen while ambulating. If a patient needs to breathe oxygen even while resting, they will be given a stationary oxygen generating unit in their home which can be set to produce 0 to 5 lpm of 93% oxygen. Generally, the units today are manually set by the patient to the prescribed flowrate. If a patient requires oxygen while ambulating, they will typically carry small high pressure oxygen cylinders or small refillable liquid oxygen dewars. Recently, small portable oxygen generators have also been introduced into the market but they suffer from drawbacks of being significantly heavier and short battery life. These devices also would be manually set by the patient to deliver oxygen at the prescribed flow rate. Due to the expense of providing oxygen in small cylinders as well as dewars for ambulation, the need to conserve the oxygen flow and efficiently utilize what was available was addressed by the development of oxygen conserving devices. These devices only deliver short pulses of oxygen at the beginning of the patients inhalation. By not delivering oxygen during exhalation or the later period of inhalation, the oxygen which would have had no impact on increasing the patient's oxygen saturation is conserved. There now exists both pneumatic and electronic oxygen conserving devices which can achieve oxygen conserving ratios from 2:1 to 6:1 compared to the delivery of continuous oxygen flow. The higher conservation ratios can only be achieved by the electronic devices since they can be programmed to skip breaths so that oxygen pulse is only delivered every other breath. Electronic devices cannot be used on all ambulating patients since their high conservation ratios can actually result in poor oxygen saturation for the patient particularly during periods of high amublation.

Pressure sensing of the onset of inhalation in electronic oxygen conservers is currently done in one of two ways:

1. Some designs require that a dual lumen cannula is used in which one of the lumens is dedicated to pressure sensing while the other is dedicated to the supply of oxygen. This design is meant to be more sensitive to the onset of inhalation but suffers from the drawback of only being able to deliver oxygen to one of the nasal passages.

2. Other designs will use a single lumen cannula that typically have a pressure sensor connected to the T piece below the two nasal prongs. Overall pressure drop associated from inhalation is sensed from both nasal passages and oxygen is then delivered to both nasal passages.

Both designs suffer from the drawback that if one of the patient's nasal passages is blocked, it will interfere with the detection and delivery of oxygen.

The idea of continuous oxygen flow adjustment to maintain patient saturation has existed for over 50 years. U.S. Pat. No. 2,414,747 by Kirschbaum (1947) discloses a method and apparatus for controlling oxygen content of the blood of living animal. The method used an ear oximeter, which produced a signal to control the fraction of inspired oxygen (FlO2).

U.S. Pat. No. 4,889,116 by Taube in 1986 describes an adaptive controller, which utilizes a pulse oximeter to measure blood oxygen saturation ($SpO_2$). This measurement would be used to calculate the necessary FlO2 to maintain a preset saturation level.

U.S. Pat. No. 5,365,922 by Raemer describes a closed loop non-invasive oxygen saturation control system which uses an adaptive controller for delivering a fractional amount of oxygen to a patient. Features of the control algorithm include a method for recognizing when pulse oximeter values deviate significantly from what should be expected. At this point the controller causes a gradual increase in the fractional amount of oxygen delivered to the patient. The feedback control means is also disconnected periodically and the response of the patient to random changes in the amount of oxygen delivered is used to tune the controller response parameters.

U.S. Pat. No. 5,682,877 describes a system and method for automatically selecting an appropriate oxygen dose to maintain a desired blood oxygen saturation level is disclosed. The system and method are particularly suited for use with ambulatory patients having chronic obstructive lung disease or other patients requiring oxygenation or ventilation. In one embodiment, the method includes delivering a first oxygen dose to the patient while repeatedly sequencing through available sequential oxygen doses at predetermined time intervals until the current blood oxygen saturation level of the patent attains the desired blood oxygen saturation levels. The method then continues with delivering the selected oxygen dose to the patient so as to maintain the desired blood oxygen saturation level.

U.S. Pat. No. 6,192,883 B1 describes an oxygen control system for supplying a predetermined rate of flow from an oxygen source to a person in need of supplemental oxygen comprising in input manifold, an output manifold and a plurality of gas conduits interconnecting the input manifold to the output manifold. The oxygen source is arranged in flow communication with the input manifold, and a needle valve is positioned in flow control relation to each of the conduits so as to control the flow of oxygen from the input manifold to the output manifold. A plurality of solenoid valves, each having a first fully closed state corresponding to a preselected level of physical activity of the person and a second, fully open state corresponding to another preselected level of physical activity of the person, are positioned in flow control relation to all but one of the conduits. Sensors for monitoring the level of physical activity of the person are provided, along with a control system that is responsive to the monitored level of physical activity, for switching the solenoids between the first state and the second state. A method for supplying supplemental oxygen to a person according to the level of physical activity undertaken by that person is also provided.

World Patent application No. WO 02/056931 A2 by Tyomkin et al. describes a method for controlling flow of gas to a patient by measuring of a preselected dissolved substance in the blood stream of a patient. The amount of gas is regulated to maintain the preselected dissolved substance above a desired value.

All the patents discussed above are based on controlling a continuous flow of oxygen. There are also patents which have described control algorithms for pulse dose oxygen devices such as the oxygen conserver.

U.S. Pat. No. 6,470,885 B1 describes a method and apparatus for controlling oxygen delivery to a person is disclosed. In one embodiment, the method includes receiving a goal blood-oxygen saturation level, measuring an actual saturation level of the person, determining a breath rate of the person, sensing a period of inhalation by the person, and delivering oxygen during inhalation by moving a valve to an oxygen delivery position for a calculated period of time based upon the actual saturation level as compared to the goal level of the person's blood-oxygen content. One embodiment of an apparatus comprises an open-loop breathing system including a control valve for controlling the flow of oxygen from a source to the person, a pressure sensor for detecting a period of inhalation, an oximeter for measuring actual blood-oxygen saturation, and a processor for calculating the time the valve needs to be maintained in an open position to deliver oxygen.

U.S. Pat. No. 6,629,525 B2 describes a portable oxygen concentrator system adapted to be transported by a user. The portable oxygen concentrator system includes an energy source, an air separation device powered by the energy source and adapted to convert ambient air into concentrated oxygen gas for the user, at least one sensor adapted to sense one or more conditions indicative of the oxygen gas needs of the user, and a control unit interrelated with the air separation device and the at least one sensor to control the air separation device so as to supply an amount of oxygen gas equivalent to the oxygen gas needs of the user based at least in part upon the one or more conditions sensed by the at least one sensor.

U.S. Pat. No. 5,865,174 describes an apparatus which conserves oxygen delivered from a supply to a patient through a cannula by providing oxygen delivery selectively in accordance with the physiological requirements and current breathing pattern of the patient. Oxygen flow is set at a prescribed flow rate from the supply by a regulator. An oxygen conserving unit includes a controller that operates responsive to timed relationships among pressure signals determined by a fuzzy logic program to deliver oxygen to the patient by opening a valve when a sensed pressure in the patient's nasal passage reaches a threshold level and when the controller determines that the reaching of the threshold is indicative of an inhalation cycle. The controller is further operative to adjust the time period that oxygen is delivered to the patient in accordance with a programmed relation to meet the dynamically changing needs of the patient. The apparatus further includes features which provide fast response, conservation of the energy from a battery power source and both visual and audio indicators to provide indications of alert and alarm conditions. The apparatus further provides control by the user through a single manually actuated switch, and mechanical interconnection with the switch and valve to assure continuous flow when the switch is set to a continuous flow setting.

U.S. Pat. No. 6,532,958 B1 describes methods and systems for supplying supplemental oxygen to patients for use in sub-acute care which maintains healthy blood oxygen content in the patients by controlled dosing of oxygen with a measured response to the patient's actual blood oxygen content are disclosed. The dosing can be provided by simple ON/OFF control over the delivery of oxygen or the amount of oxygen delivered to the patient with each inhalation can be varied in response to the patient's need as determined by a more sophisticated control scheme, such as PID loop control algorithm, that utilizes the difference between the patient's actual blood oxygen content and a target blood oxygen content and/or trends in the blood oxygen content. The systems and methods are particularly directed at patients receiving supplemental oxygen in a sub-acute care environment.

U.S. Pat. No. 6,186,142 B1 describes methods and systems for supplying respiratory oxygen to patients when the patients are inhaling are disclosed. The methods and systems may rely on delivery devices that are selectively placed in fluid communication with either a respiration sensor or a source of oxygen. The methods and systems may actively monitor for exhalations, as well as monitor for oxygen in the oxygen source. The respiration sensor may preferable be a flow sensor.

U.S. Pat. No. 6,371,114 B1 describes methods and systems for supplying supplemental oxygen to patients for use in sub-acute care which maintains healthy blood oxygen content in the patients by controlled dosing of oxygen with a measured response to the patient's actual blood oxygen content are disclosed. The dosing can be provided by simple ON/OFF control over the delivery of oxygen or the amount of oxygen delivered to the patient with each inhalation can be varied in response to the patient's need as determined by a more sophisticated control scheme, such as PID loop control algorithm, that utilizes the difference between the patient's actual blood oxygen content and a target blood oxygen content and/or trends in the blood oxygen content. The systems and methods are particularly directed at patients receiving supplemental oxygen in a sub-acute care environment.

A major flaw with current oxygen generating devices is the fact that a patient's ideal need for oxygen varies with time both in the short term as a result of varying exertion and in the long term as result of improvement or deterioration in health. When a doctor prescribes a fixed flow rate of oxygen for a patient they are mainly concerned with ensuring that the patient's blood saturation does not drop below an $SpO_2$ value of 88%. They are not concerned if the patient is receiving too much oxygen, for example while resting. The prescription is therefore more likely to be conservative in nature so as to ensure oversaturation as opposed to undersaturation. It is generally believed and accepted by doctors that too much oxygen flow is harmless whereas too little can be harmful. This method of oxygen prescription is prone to error as proved by a recent study by Fussell et al. (Respiratory Care—February 2003, Vol. 48 No. 2). In this study, 20 patient's blood saturation levels were monitored continuously using pulse oximeters to confirm if their oxygen prescription adequately maintained their saturation. The conclusion of the study was that there was a poor relationship between conventional oxygenation assessment method and continuous ambulatory oximetry during LTOT screening with COPD patients.

Generally, after a second doctor visit which is typically scheduled 3 months after the prescription is initially made, patients may be asked to return to the doctor anywhere between 6 to 12 months. During that time if the patient's health and hence need for oxygen changes, a significant time may pass before it is detected by the doctor or home care provider.

Conservative (high) oxygen prescriptions, while they may be harmless to the patient, are needlessly expensive resulting in increase in the cost of providing oxygen for the home care provider as well as increase the hurdles that battery and oxygen separation technology have to overcome to develop a portable oxygen generating unit that can last a reasonable amount of time and weigh less than what is believed to be the upper acceptable limit of 10 lbs.

Many COPD patients who use stationary oxygen concentrators in their homes are financially impaired and are concerned about the power costs of continuously running an oxygen concentrator. In many cases this has led to a compliance issue where the patient refuses to switch on the concentrator and follow the therapy as prescribed by the doctor in order to save on their electricity bill. Current oxygen concentrator designs will typically produce the maximum flowrate possible which is typically 5 lpm. If a patient's resting prescription is 2 lpm, the patient will set a flow rate through their cannula to the required flow and the excess oxygen that is being produced is vented from the concentration into the room. There is potential to reduce power consumption by only producing the amount oxygen that the patient needs in a real time basis. Many oxygen therapy patients can spend a significant amount of their time while resting with blood saturation levels that are acceptable.

It is an object of the present invention to provide an oxygen delivery system which supplies oxygen flow at a rate that a patient needs on a real time basis as determined by their heart rate and blood oxygen saturation level.

It is another object of the present invention to provide both a system and methods for optimal conserving of oxygen deliver to a patient using dual sensor means in an oximeter.

With these and other objects in mind, the invention is hereinafter described in detail, the novel features thereof being particularly pointed out in the appended claims.

SUMMARY OF THE INVENTION

One embodiment of the invention is an apparatus with dual sensing means for automatically controlling and conserving the delivery of oxygen to a patient comprising:
 an oxygen supply;
 oximeter means having a first non-invasion sensor to measure blood hemoglobin saturation ($SpO_2$) of a patient and a second non-invasive sensor to measure the pulse rate of the patients;
 means for providing or accepting as input by a user a setpoint level of a desired blood saturation for the patient;
 first control means adapted for identifying the pulse rate and providing a pulse signal;
 second control means adopted for identifying an error signal representing the difference between the setpoint level and the $SpO_2$ signal; and
 means for responding to the pulse signal and the error signal to adjust the oxygen supply to provide a desired amount of oxygen to the patient.

Another embodiment of the invention relates to a method for delivery and controlling oxygen to a patient from an oxygen supply which effectively conserving said oxygen supply, comprising the steps of:
 a) providing a supply of oxygen;
 b) providing or accepting as input by a user a desired setpoint signal for the blood hemoglobin saturation of a patient;
 c) measuring the blood hemoglobin saturation ($SpO_2$) in the patient and providing said measured value as an $SpO_2$ signal;
 d) generating an error signal by substrating the setpoint signal from the measured blood hemoglobin saturation signal;
 e) measuring the pulse rate on the patent and providing said measure as a pulse signal;
 f) generating a running controlling signal by combining the error signal and the pulse signal through a mathematical operation; and
 g) adjusting a deliverable amount of oxygen to the patient in response to controlling signal of step f).

Another embodiment of this invention is:

An apparatus with dual sensing means for automatically controlling and conserving the delivery of oxygen to a patient comprising:
 an oxygen supply generator;
 oximeter means having a first non-invasion sensor to measure blood hemoglobin sensor to measure the pulse rate of the patient;
 means for providing or accepting as input by a user a setpoint level of a desired blood saturation for the patient;
 first control means adapted for identifying a pulse rate and providing a pulse signal;
 second control means adopted for identifying a first error signal representing the difference between the set point level and a signal representing the measurement of the blood saturation;
 means for responding to the pulse signal and the first error signal to provide an oxygen flow setpoint signal;
 means for identifying a flow from the oxygen supply generator to provide an oxygen flow signal;
 means adapted for identifying a second error signal representing the difference between the oxygen flow signal and the oxygen flow setpoint signal; and
 means for responding to the second error signal to modulate variables of the oxygen generator to a desired level.

Another method for delivery and controlling oxygen to a patient from an oxygen supply which effectively conserving said oxygen supply, comprising the steps of:
 a) providing a supply of oxygen from an oxygen generator;
 b) providing or accepting as input by a user a desired setpoint signal for the blood hemoglobin saturation of a patient;
 c) measuring the blood hemoglobin saturation ($SpO_2$) in the patient and providing said measured value as an $SpO_2$ signal;

d) generating a first error signal by substrating the setpoint signal from the measured blood hemoglobin saturation signal;

e) measuring the pulse rate on the patent and providing said measure as a pulse signal;

f) generating an oxygen flow setpoint signal by combining the error signal and the pulse signal through a mathematical operation;

g) measuring the oxygen flow from the oxygen generator and providing an oxygen flow signal;

h) generating a second error signal by substrating the oxygen flow setpoint signal from the oxygen flow signal; and i) adjusting a deliverable amount of oxygen to the patient in response to the second error signal of step h).

Due to advances in pulse oximetry technology, pulse oximeters of the invention measure both heart pulse rate and blood saturation and can be very small in size and could be easily carried continuously by the patient. Wrist watch sized devices can have a sensor which has to be worn on the patient's finger tip. This can make wearing a pulse oximeter on a continuous basis, awkward and uncomfortable in the sense that it would interfere with usual tasks that a patient uses their fingers for, e.g. eating, typing, writing, etc. In accordance wit the invention, a comfortable and convenient location for a pulse oximeter sensor is described which should help make the continuous monitoring of blood saturation a practical possibility. This is critical for the application of an oxygen delivery method, which supplies oxygen flow at the rate a patient needs on a real time basis as determined by their heart rate and blood oxygen saturation level.

The oxygen generating a portable or stationary apparatus where the power supplied to the generator is varied and hence the amount of oxygen produced is directly linked to the patient's need for oxygen as measured by both heart rate and blood saturation. Since only the amount of oxygen required is generated, this unit may consume less power and thus last longer than existing portable units which consume a fixed amount of power independent of the amount of oxygen that the patient actually needs. Also during periods of exertion, this device will more adequately and automatically serve the patient's need for oxygen and hence prevent them from desaturation. Two aspects of the invention are:

1. Using heart rate as an early warning mechanism for the patient's impending need for more or less oxygen. This should address some of the time lag issues associated with devices that only measure blood saturation. Devices which only depend on blood oxygen saturation can be inadequate in adequately maintaining blood oxygen levels for two reasons:

A. By the time blood oxygen level begins to drop, the process of desaturation may have gathered considerable momentum such that it takes time for the increase in oxygen flow to return the blood saturation level back to a normal level.

B. Due to the fact that oxygen levels are typically being measured at the finger tip, it takes a period of time for the blood which has dropped in saturation to reach the finger tips compared to other parts of the body. Hence vital organs may be receiving blood with deficient oxygen levels while the blood at the finger tips is still of an acceptable oxygen saturation level.

2. Varying the actual amount of oxygen produced as opposed to just adjusting the flow with a control valve whereby only a fraction of the produced oxygen is utilized and hence energy is wasted. For example, patients can breathe room air for significant periods of time while resting. During these periods the oxygen generator will be switched off to conserve power consumption.

Figure 1:
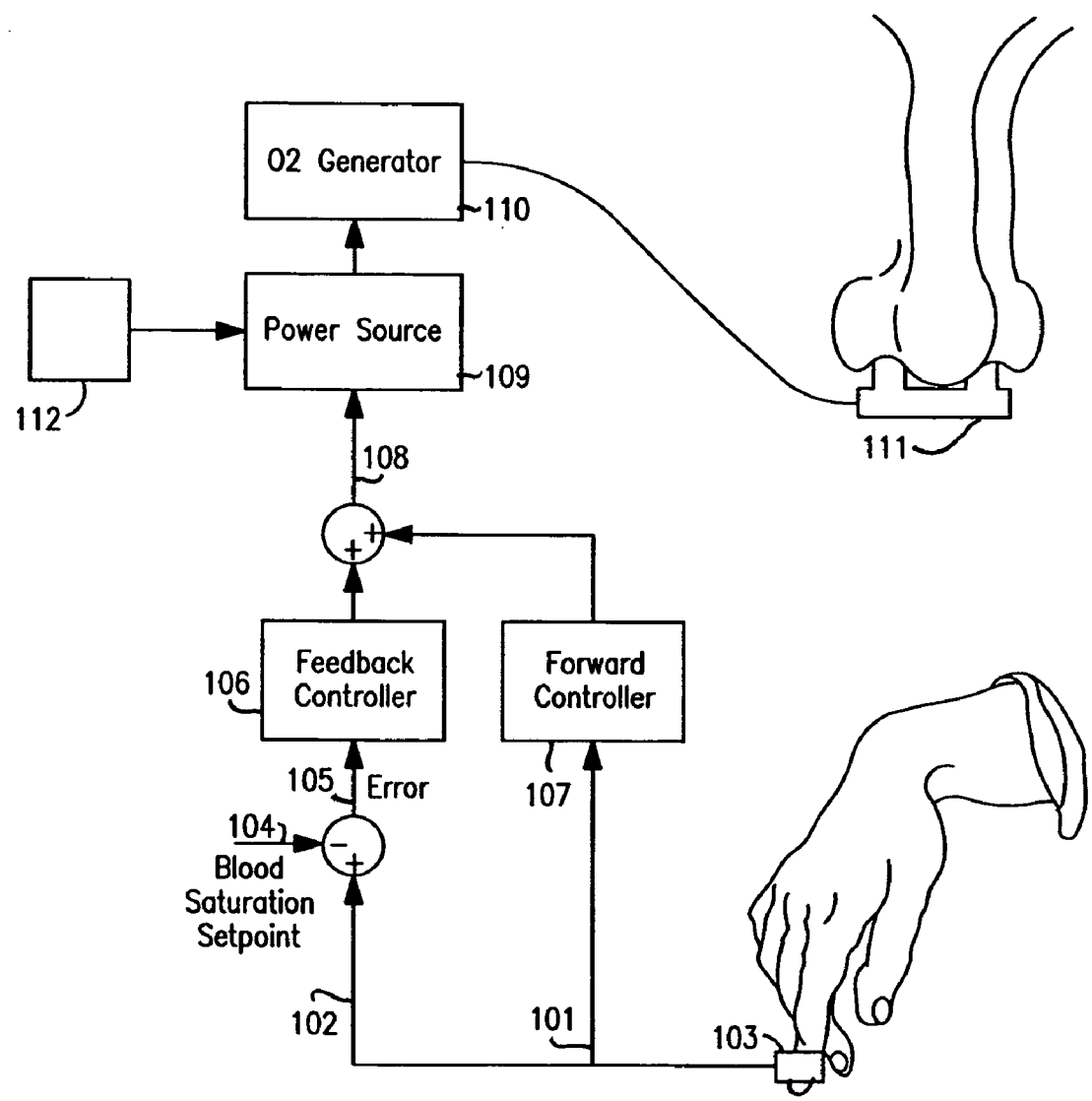
FIG. 1 is a block diagram of an embodiment of the present invention using an oximeter having dual sensors.

A preferred embodiment of the control delivery mechanism of the invention is illustrated in FIG. 1. A patient's heart rate 101 and blood saturation 102 are continuously measured via a pulse oximeter 103.

A desired blood saturation level, or setpoint 104 is subtracted from the blood saturation measurement 102 via pulse oximeter 103 to determine an error signal 105. This error signal is an indication of how far the blood saturation level is from its desired value. The error signal 105 is sent to a conventional slow-acting feedback controller 106 that determines the fine adjustments needed to drive the blood saturation level towards the desired value, eventually eliminating any offset between the blood saturation level and the desired value.

A second controller, a fast acting feedforward controller 107, takes as its input the measured pulse rate 101 and determines what action should be taken to prevent the blood saturation level from changing suddenly in the face of an increase or decrease in physical activity.

A conventional feedback controller known in the art takes corrective action based on a change observed in the process variable under control. It is reactionary. By contrast, a conventional feedforward, also known in the art, takes corrective action when a change is observed in a variable known to change prior to the variable being controlled. It is pro-active in nature. The best way to understand it would be through example. Suppose you are in the shower and the water suddenly turns cold, so you turn the shower knob to increase the flow of hot water. That is feedback control. Suppose you are in the same shower and you hear the toilet flush in another room. You know that that usually preceeds the water turning ice-cold so you make an adjustment to the shower knob to prevent a decrease in water temperature. That is feedforward control.

The outputs of the feedback and feedforward controllers are then combined (added) to form an input signal 108 to the power source 109 of the oxygen generator 110. Preferably, the power source will have a variable frequency drive to allow the oxygen production rate to be modulated over a continuous range of values as opposed to discrete values; however, alternate embodiments should be used.

The oxygen generator 110 generates oxygen in an amount that is dependant on the power supplied by the power source 109. This oxygen is delivered to the patient via a tube connected to a cannula 111.

Controllers can be implemented in a number of different ways. They can consist of conventional analog electrical components in a known type of circuit designed to provide the desired relationship between input and output current (usually 4–20 mA). They may also be built from conventional mechanical devices designed to provide the desired relationship between input and output pneumatic signals (usually 3–15 psig). The relationships of the signals may also be programmed into a conventional type of computer provided A/D and D/A (analog to digital and digital to analog) converts which can be used to interface the computer with the analog input and output lines. Preferably, since the third method is cost effective, the method envisioned for carrying out the control policy for this invention should be used.

Since the advent of computer based control, many algorithms have been developed for automatic control. The simplest of these algorithms mimic the action of classical analog controllers (i.e. Proportional+Integral, or PI control for the feedback portion and a lead-lag dynamic for the feedforward portion). Being the simplest control algorithms, they are preferred over others, nevertheless, other more advanced algorithms may be used. Model predictive control algorithms may be used to provide more optimal control if necessary. Adaptive control techniques could be used if it is found that the patient's response to oxygen therapy is highly variable. Even methods based on artificial intelligence (such as neural networks, expert systems, or fuzzy logic) could be used without changing the general nature of the invention.

Because the main concept of the invention is around the delivery of the proper amount of oxygen to the patient under normal system functioning a failsafe mechanism 112 is used to activate an alarm upon sensoring a sensor failure or computer failure. The alarm could be in any form such as a warning light, readout display, buzzer, etc. After the warning has been noted and the default corrected, the system can then be resumed.

Figure 2:
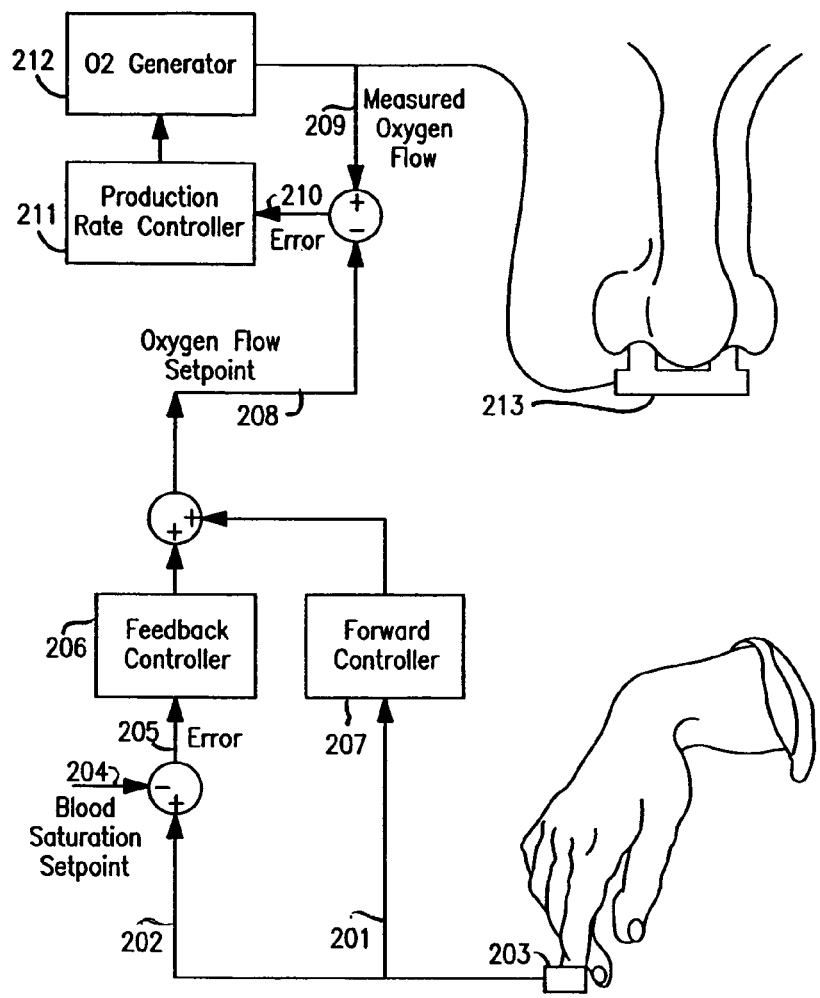
FIG. 2 is a block diagram of another embodiment of the present invention using an oximeter with cascading control system.

Another embodiment of the invention is illustrated in FIG. 2, and is similar to the embodiment illustrated in FIG. 1 with the addition of a cascade control system. A patient's heart rate 201 and blood saturation 202 are continuously measured via a pulse oximeter 203. A desired blood saturation level, or setpoint 204 is subtracted from the blood saturation measurement 202 via pulse oximeter 203 to determine an error signal 205. This error signal is an indication of how far the blood saturation level is from its desired value. The error signal 205 is sent to a conventional slow-acting feedback controller 206 that determines the fine adjustments needed to drive the blood saturation level towards the desired value, eventually eliminating any offset between the blood saturation level and the desired value. A second controller, a fast acting feed forward controller 207, takes as its input the measured pulse rate 201 and determines what action should be taken to prevent the blood saturation level from changing suddenly in the face of an increase or decrease in physical activity. In this embodiment the output signal of the blood saturation controllers 208 is an oxygen production rate setpoint signal rather than a power signal as before. There is an additional sensor that measures the flowrate of oxygen 209. The setpoint signal 208 is subtracted from the measured production rate 209 to generate an error signal 210. The error signal is fed to a production rate controller 211 that modulates some variable of the $O_2$ generator 212 in order to drive the production rate towards its target value. Any variable may be selected so long as it has a measurable impact on production rate. The simplest choice would be to allow the production rate controller to modulate the $O_2$ generator power input. Other choices should be used depending on the design of the oxygen generator.

Figure 3:
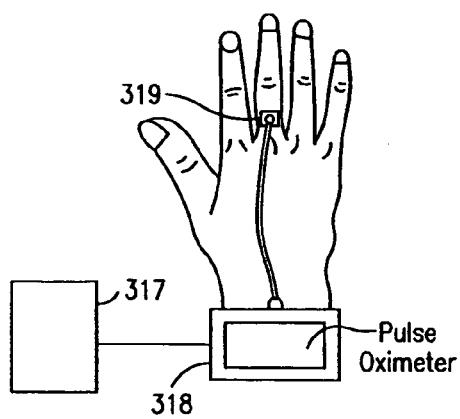
FIG. 3 is a block diagram showing the placement of a pulse oximeter and its probe on a patient's hand.

FIG. 3 shows an apparatus 317 of the type shown in FIGS. 1 and 2 that could be designed to receive inputs such as oxygen saturation and heart rate from a pulse oximeter 318. These inputs would be used in algorithm to determine the correct flow rate of oxygen to be delivered to the patient. In FIG. 3, the pulse oximeter 318 may be worn on the patient's wrist. The pulse oximeter probe 319 would be designed as a ring shaped device which is worn at the base of one of the patient's fingers. It is understood that this location is ideal compared to a place for sensing oxygen saturation on a finger tip. However, in applications where the patient is expected to wear the pulse oximeter on a continuous basis, this location serves as a far more user friendly and practical place to have a probe which does not interfere with daily activities requiring the user's finger tips.

Specific features of the invention are shown in one or more of the drawings for convenience only, as each feature may be combined with other features in accordance with the invention. Alternative embodiments will be recognized by those skilled in the art and are intended to be included within the scope of the claims.

What is claimed:

1. An apparatus with dual sensing means for automatically controlling and conserving the delivery of oxygen to a patient comprising:
   an oxygen supply generator;
   oximeter means having a first non-invasive sensor to measure blood hemoglobin saturation ($SpO_2$) of a patient and a second non-invasive sensor to measure the pulse rate of the patient;
   means for providing a setpoint level of a desired blood saturation for the patient;
   first control means adapted for identifying a pulse rate and providing a pulse signal;
   second control means adapted for identifying a first error signal representing the difference between the setpoint level and a signal representing the measurement of the blood saturation;
   means for responding to the pulse signal and the first error signal to provide an oxygen flow setpoint signal;
   means for identifying a flow from the oxygen supply generator to provide an oxygen flow signal;
   means adapted for identifying a second error signal representing the difference between the oxygen flow signal and the oxygen flow setpoint signal; and
   means for responding to the second error signal to modulate variables of the oxygen generator to a desired level.

2. The apparatus of claim 1 wherein at least one of the first and second control means is a controller comprising an operating system selected from the group consisting of analog electrical components providing electrical input and output current signals; mechanical components providing pneumatic input and output signals; computers providing analog to digital and digital to analog converters with analog input and output lines; and artificial intelligence providing input and output signals.

3. The apparatus of claim 1 wherein the oximeter means comprises a pulse oximeter adapted to be worn on a patient's wrist and having a probe from the oximeter with a ring shape adapted to be worn at the base of one of the patient's fingers.

4. The apparatus of claim 1 further comprising an alarm means adapted to indicate any default in the operation of the apparatus.

5. A method for delivering and controlling oxygen to a patient from an oxygen supply while effectively conserving said oxygen supply, comprising the steps of:
   a) providing a supply of oxygen from an oxygen generator;
   b) providing a desired setpoint signal for the blood hemoglobin saturation of a patient;
   c) measuring the blood hemoglobin saturation ($SpO_2$) in the patient and providing said measured value as an $SpO_2$ signal;

d) generating a first error signal by subtracting the setpoint signal from the measured blood hemoglobin saturation signal;
e) measuring the pulse rate on the patient and providing said measure as a pulse signal;
f) generating an oxygen flow setpoint signal by combining the first error signal and the pulse signal;
g) measuring the oxygen flow from the oxygen generator and providing an oxygen flow signal;
h) generating a second error signal by subtracting the oxygen flow setpoint signal from the oxygen flow signal; and
i) adjusting a deliverable amount of oxygen to the patient in response to the second error signal of step.

6. The method of claim 5 wherein an oximeter is used to measure both the blood hemoglobin saturation and the pulse rate.

7. The method of claim 5 wherein the $SpO_2$ signal and pulse signal are provided by feed controllers wherein at least one of the controllers comprise analog electrical components providing electrical input and output current signals; mechanical components providing pneumatic input and output signals; computers providing analog to digital and digital to analog converters with analog input and output lines; and artificial intelligence providing input and output signals.

8. The method of claim 5 further comprising the step of:
j) indicating any default in any of the signals.

* * * * *